United States Patent [19]

Mita et al.

[11] Patent Number: 4,778,916

[45] Date of Patent: Oct. 18, 1988

[54] PREPARATION PROCESS OF α-L-ASPARTYL-L-PHENYLALANINE METHYL ESTER OR HYDROCHLORIDE THEREOF

[75] Inventors: Ryuichi Mita; Toshio Katoh, both of Kawasaki; Chojiro Higuchi, Kamakura; Takeshi Oura, Zushi; Akihiro Yamaguchi, Kamakura, all of Japan

[73] Assignee: Mitsui Toatsu Chemicals, Inc., Tokyo, Japan

[21] Appl. No.: 122,583

[22] Filed: Nov. 17, 1987

Related U.S. Application Data

[63] Continuation of Ser. No. 63,737, Jun. 17, 1987, abandoned, which is a continuation of Ser. No. 836,131, Mar. 4, 1986, abandoned.

[30] Foreign Application Priority Data

Mar. 26, 1985 [JP] Japan ................................. 60-59557
Mar. 29, 1985 [JP] Japan ................................. 60-66095

[51] Int. Cl.$^4$ .................... C07C 103/52; C07C 102/00
[52] U.S. Cl. ........................................ 560/40; 560/41; 530/801; 426/548
[58] Field of Search ................ 546/247; 426/548; 560/38, 40, 41; 548/478; 549/477, 253; 530/801; 562/445

[56] References Cited

U.S. PATENT DOCUMENTS

| | | | |
|---|---|---|---|
| 3,879,372 | 4/1975 | Boesten | 560/40 |
| 3,933,781 | 1/1976 | Bachman et al. | 560/41 |
| 4,021,418 | 5/1977 | Takemoto et al. | 530/337 |
| 4,071,511 | 1/1978 | Takemoto et al. | 530/335 |
| 4,088,649 | 5/1978 | Smith et al. | 544/385 |
| 4,153,737 | 5/1979 | Berg et al. | 426/548 |
| 4,579,747 | 4/1986 | Sugiyama et al. | 426/548 |
| 4,634,790 | 1/1987 | Shinohara et al. | 560/40 |

FOREIGN PATENT DOCUMENTS

| | | |
|---|---|---|
| 0092933 | 11/1983 | European Pat. Off. |
| 0127411 | 5/1984 | European Pat. Off. |
| 86301681 | 8/1987 | European Pat. Off. |
| 1370 | 4/1971 | Japan |
| 96557 | 2/1973 | Japan |
| 113841 | 12/1976 | Japan |
| 40069 | 12/1976 | Japan |
| 82752 | 1/1978 | Japan |
| 26133 | 6/1980 | Japan |
| 130846 | 1/1984 | Japan |
| 219258 | 1/1984 | Japan |
| 225152 | 2/1984 | Japan |
| 225153 | 4/1984 | Japan |
| 50200 | 6/1985 | Japan |
| 174799 | 1/1986 | Japan |
| 1359123 | 7/1974 | United Kingdom |
| 1464140 | 2/1977 | United Kingdom |
| 2133409 | 7/1984 | United Kingdom |

OTHER PUBLICATIONS

Chemical Abstracts, 105:153551s.

*Primary Examiner*—John Kight
*Assistant Examiner*—Nathan M. Nutter
*Attorney, Agent, or Firm*—Fisher, Christen & Sabol

[57] ABSTRACT

The present invention relates to a process for preparing α-L-aspartyl-L-phenylalanine methyl ester or its hydrochloride. α-L-aspartyl-L-phenylalanine methyl ester or its hydrochloride is prepared by a process comprising: condensating N-formyl-L-aspartic acid anhydride and L-phenylalanine in water or in water containing methanol at a pH in the range of 7–12 to form N-formyl-α-L-aspartyl-L-phenylalanine; acidifying the reaction mixture successively with hydrochloric acid in the presence of methanol without isolating the N-formyl-α-L-aspartyl-L-phenylalanine so as to bring it into contact with hydrochloric acid in the presence of methanol for reaction and thereby to deposit α-L-aspartyl-L-phenylalanine methyl ester hydrochloride; separating the α-L-aspartyl-L-phenylalanine methyl ester hydrochloride; and neutralizing said hydrochloride as required.

2 Claims, No Drawings

PREPARATION PROCESS OF α-L-ASPARTYL-L-PHENYLALANINE METHYL ESTER OR HYDROCHLORIDE THEREOF

This application is a continuation of application Ser. No. 063,737, filed June 17, 1987, which is a continuation of applicaton Ser. No. 836,131, filed Mar. 4, 1986, now both abandoned.

This invention relates to a preparation process of α-L-aspartyl-L-phenylalanine methyl ester or its hydrochloride. More specifically, this invention provides a process for preparing α-L-aspartyl-L-phenylalanine methyl ester or its hydrochloride which process comprises: condensating N-formyl-L-aspartic acid anhydride and L-phenylalanine in water at a pH in the range of 7–12 to form N-formyl-α-L-aspartyl-L-phenylalanine; acidifying the reaction mixture with hydrochloric acid in the presence of methanol without isolating the N-formyl-α-L-aspartyl-L-phenylalanine so as to bring it into contact with hydrochloric acid in the presence of methanol for reaction and thereby to precipitate α-L-aspartyl-L-phenylalanine methyl ester hydrochloride; separating the α-L-aspartyl-L-phenylalanine methyl ester hydrochloride; and neutralizing said hydrochloride as required. Further, this invention provides another process for preparing α-L-aspartyl-L-phenylalanine methyl ester or its hydrochloride which process comprises: condensating N-formyl-L-aspartic acid anhydride and L-phenylalanine in water containing methanol in an amount of 6 moles or less per mol of the L-phenylalanine at a pH in the range of 7–12 to form N-formyl-α-L-aspartyl-L-phenylalanine; acidifying the reaction mixture with hydrochloric acid without isolating the N-formyl-α-L-aspartyl-L-phenylalanine so as to bring it into contact with hydrochloric acid in the presence of methanol for reaction and thereby to precipitate α-L-aspartyl-L-phenylalanine methyl ester hydrochloride; separating the α-L-aspartyl-L-phenylalanine methyl ester hydrochloride; and neutralizing said hydrochloride as required.

BACKGROUND OF THE INVENTION

α-L-aspartyl-L-phenylalanine methyl ester (hereinafter abbreviated as α-APM) is a compound commonly referred to as "Aspartame". It has a sweetness approximately 200 times that of cane sugar and thus is in ever-increasing demand as a diet sweetening agent.

Numerous chemical preparation processes of α-APM have so far been disclosed. There may be cited a variety of processes, for example, (1) a process which comprises condensating the hydrochloride of aspartic acid anhydride and L-phenylalanine methyl ester (Japanese Patent Publication No. 40069/1976, etc.), (2) a process which comprises condensating N-protective aspartic acid anhydride and L-phenylalanine methyl ester followed by de-protection (Japanese Patent Laid-Open Nos. 1370/1971 and 113841/1976, etc.), (3) a process which comprises reacting N-protective aspartic acid-β-benzyl ester with L-phenylalanine methyl ester in the presence of a condensating agent followed by de-protection (Japanese Patent Laid-Open No. 130846/1984) and (4) a process which comprises reacting N-carboxy-aspartic acid anhydride and L-phenylalanine methyl ester (Japanese Patent Laid-Open No. 96557/1973).

However, all of these processes employ L-phenylalanine methyl ester as one of the raw materials, requiring complex steps of methyl-esterification of L-phenylalanine prior to the reaction with the active derivatives of aspartic acid.

Moreover, further investigation has revealed that L-phenylalanine methyl ester is a compound in which its two free molecules in a solution are liable to condensate and cyclize to 2,5-dibenzyl-diketopiperazine. This face may be responsible for various disadvantages taking place in the industrial production of α-APM.

Accordingly, it is desirable to develop a process which is free of these disadvantages in the production of α-APM, i.e., a process in which L-phenylalanine methyl ester is not used as a raw material.

As a process for preparing α-APM which does not employ L-phenylalanine methyl ester, there has been disclosed a process for preparing α-APM which comprises condensating N-formyl aspartic acid anhydride with L-phenylalanine in glacial acetic acid to form N-formyl-α-L-aspartyl-L-phenylalanine, deformylating the N-formyl-α-L-aspartyl-L-phenylalanine to form α-L-aspartyl-L-phenylalanine, and esterifying said compound in methanol (Japanese Patent Publication No. 26133/1980), and a process in which the esterification step of α-L-aspartyl-L-phenylalanine to α-APM is improved (Japanese Patent Laid-Open No. 82752/1978).

However, since the former process brings about the estrification reaction in a substantailly non-aqueous solution, the reaction has practically no freedom of selectivity so that not only the intended esterification but also the estrification of its β-carboxyl group of aspartic acid as well as the diesterification takes place to a large extent. Therefore, the process suffers such disadvantages as low yield of α-APM.

The latter process, which is established by improving the former process, bring about the methyl-esterification of α-L-aspartyl-L-phenylalanine in the presence of a considerable amount of water and the α-APM thus formed is deposited as its hydrochloride which is hardly soluble in the reaction system, thereby increasing the selectivity toward α-APM. However, the yield of isolation of α-APM in the latter process is at most 50–60% (based on α-L-aspartyl-L-phenylalanine) and thus is insufficient.

As another process in which L-phenylalanine methyl ester is not used, there has recently been disclosed a process for preparing α-APM which comprises condensating the N-carboxylic acid anhydride of L-aspartic acid-β-methyl ester and L-phenylalanine to produce α-L-aspartyl-L-phenylalanine-β-methyl ester and subjecting said compound to intramolecular transesterification in an aqueous hydrochloric acid solution containing methanol (Japanese Patent Laid-Open Nos. 225152/1984 and 225153/1984).

However, in this process, the esterification for producing L-aspartic acid-β-methyl ester is poor in selectivity and thus is low in yield. Further, its N-carboxylic acid anhydride, which is produced by reacting L-aspartic acid-β-methyl ester with phosgene, is liable to polymerize by being brought into contact with a base or by other causes. Therefore, this process is disadvantageous from the industrial viewpoint.

As has been described above, the conventional preparation processes of α-APM have several stages of complicated steps and have merits and demerits in the stability of its intermediates and in yield or in safety. Thus, it is the existing state of art that there are no efficient processes for preparing α-APM.

Further, a new preparation process of α-APM in which α-L-aspartyl-L-phenylalanine dimethyl ester is hydrolyzed in an aqueous methanol-hydrochloric acid solution has lately been disclosed (Japanses Patent Laid-Open No. 219258/1984). According to this disclosure, the starting α-L-aspartyl-L-phenylalanine dimethyl ester is prepared by de-formylatioun and estrification of N-formyl-α-L-aspartyl-L-phenylalanine methyl ester or by condensating the N-carboxylic acid anhydride of L-aspartic acid-β-methyl ester with L-phenylalanine methyl ester. Thus, the process employs L-phenylalanine methyl ester for the preparation of the starting material and therefore involves the above-described problems.

SUMMARY OF THE INVENTION

The present inventors have made an effort to establish a process for preparing α-APM in a further efficient manner in view of the aforesaid existing state of α-APM preparation techniques, without using L-phenylalanine methyl ester which involves problems in its stability in a solution as described above. Particularly, taking into account the fact that the preparation processes of α-APM generally have, as described above, long steps from the starting material to the product of α-APM, the present inventors have made extensive investigations on an efficient process for the preparation of α-APM by simplifying the steps to the greatest possible extent.

As a result, the present inventors have found that the condensation reaction of N-formyl-L-aspartic acid anhydride and L-phenylalanine causes almost no by-production of impurities and produces the α-isomer(N-formyl-α-L-aspartyl-L-phenylalanine) in much larger amounts than the β-isomer (N-formyl-β-L-aspartyl-L-phenylalanine) in water or a water medium containing methanol. Further, when the reaction is carried out in a limited amount of condensation solvent, it has been found that the reaction mixture can be subjected to further reaction without isolating the condensation product by bringing it into contact with hydrochloric acid in the presence of methanol, thereby making it possible to produce α-APM in one reactor.

When several stages of reaction from the starting materials to the intended α-APM are carried out in one reacter, it is generally considered that a variety of impurities occuring in each reaction stage exert unfavorable effects upon the intended reaction and the quality of the product α-APM. Specifically, the condensation reaction of N-formyl-L-aspartic acid anhydride and L-phenylalanine by-produces the β-isomer in a yield of 20% or more, in addition to the intended β-isomer. Moreover, the condensation reaction mixture often contains N-formyl-L-aspartyic acid and/or its methyl ester formed by reacting N-formyl-L-aspartic acid anhydride with water and/or methanol to open its ring and, in some cases, unreacted L-phenylalanine and other compounds, forming a rather complicated system.

However, the present inventors have found that when N-formyl-L-aspartic acid anhydride and L-phenylalanine are reacted with each other in water or a water medium containing methanol and the resulting reaction mixture is then brought into contact with hydrochloric acid in the presence of methanol, the reaction including deformylation proceeds under mild conditions to form α-APM which, among other compounds formed by the reaction, precipitates exclusively out of the system as its hydrochloride without being affected by various impurities. The present invention has been completed on the basis of this discovery.

The process of the present invention has the following two process modes as the embodiment.

The first process mode comprises: condensating N-formyl-L-aspartic acid anhydride with L-phenylalanine in water at a pH in the range of 7-12 to form N-formyl-α-L-aspartyl-L-phenylalanine; acidifying the reaction mixture successively with hydrochloric acid in the presence of methanol without isolating the N-formyl-α-L-aspartyl-L-phenylalanine formed so as to bring it into contact with hydrochloric acid in the presence of methanol and thereby to precipitate α-APM hydrochloride; separating the α-APM hydrochloride; and neutralizing said hydrochloride as required, thereby preparing α-APM or its hydrochloride.

The second process mode comprises: condensating N-formyl-L-aspartic aicd anhydride with L-phenylalanine in water containing methanol in an amount of 6 equivalents or less to L-phenylalanine at a pH in the range of 7-12 to form N-formyl-α-L-aspartyl-L-phenylalanine; acidifying the reaction mixture successively with hydrochloric acid without isolating the N-formyl-α-L-aspartyl-L-phenylalanine so as to bring it into contact with hydrochloric acid in the presence of methanol and thereby to precipitate α-APM hydrochloride; separating the α-APM hydrochloride; and neutralizing said hydrochloride as required, thereby preparing α-APM or its hydrochloride.

The process of the present invention is advantageous in that L-phenylalanine can be used directly in place of L-phenylalanine methyl ester which involves problems in its stability in a solution. Besides, the process is able to produce the intended product, α-APM, from L-phenylalanine used as a raw material in one reactor.

There have been disclosed a variety of processes for producing α-APM by way of isolated intermediates. As compared with these processes, the process of the present invention can prepare α-APM without losing the expensive raw material, L-phenylalanine, and is highly efficient from the operational point of view. In addition, the β-isomer, which is by-produced in the condensation of N-formyl-L-aspartic acid anhydride with L-phenylalanine, produces various compounds through deformylation and esterification by being brought into contact with hydrochloric acid in the presence of methanol. These compounds, however, do not exert adverse effects upon the deposition of α-APM hydrochloride but move entirely to the mother liquer from which the deposited α-APM hydrochloride is separated. Therefore, if this mother liquor is subjected to hydrolysis, L-phenylalanine and L-aspartic acid are recovered as a raw material in fairly high concentrations. Accordingly, when these compounds are isolated from the mother liquor after the hydrolysis, it becomes unnecessary to submit it to a concentration operation which generally requires a substantial amount of energy.

DETAILED DESCRIPTION OF THE INVENTION

The present invention employs N-formyl-L-aspartic acid anhydride as a raw material. N-formyl-L-aspartic acid anhydride can be produced with ease by any processes known per se in the art, for example, by reacting L-aspartic acid with formic acid and acetic anhydride.

In the process of the present invention, N-formyl-L-aspartic acid anhydride is condensated with L-phenylalanine in water or water containing methanol at a pH in the range of 7-12 to form N-formyl-α-L-aspartyl-L-phenylalanine.

N-formyl-L-aspartic acid anhydride may be used in a stoichiometrical amount or more relative to L-phenylalanine, but should not be used in unduly excessive amounts. Generally, N-formyl-L-aspartic acid anhydride is used in an amount of less than 2 moles per mole of L-phenylalanine. The use of N-formyl-L-aspartic acid anhydride in an amount less than equivalent to L-phenylalanine may not raise any problems from the standpoint of reaction. It may however cause some of expensive L-phenylalanine to be left unreacted and thus is not advantageous from the economical point of view.

The condensation reaction of N-formyl-L-aspartic acid anhydride with L-phenylalanine is carried out in water or in water containing methanol. Water may be used in an amount 1-10 times by weight that of L-phenylalanine used as a raw material, in view of the fact that the resulting reaction mixture, as it is, is successively submitted to the α-APM forming reaction after the condensation reaction, and from the standpoint of reaction operation. The amount of water may preferably be 8 times by weight or less that of L-phenylalanine.

When the condensation reaction is carried out in water containing methanol, the amount of methanol used may be 6 equivalents or less based on L-phenylalanine. Any methanol amounts in excess of 6 equivalents to L-phenylalanine will cause the concentration of methanol in the successive α-APM forming step to increase and thus the solubility of α-APM hydrochloride to be increased, with the result that the yield of α-APM will unfavorably be decreased.

In the process of the present invention, the condensation of N-formyl-L-aspartic acid anhydride with L-phenylalanine is practiced in the following manner: L-phenylalanine and an alkali are dissolved or suspended in a given amount of water or water containing methanol. Then, N-formyl-L-aspartic acid anhydride is fed little by little to the resulting solution or suspension either continuously or dividedly. During the feed, an aqueous alkaline solution is added dropwise to the reaction liquid so as to ajust and maintain its pH in the range of 7-12. As the alkali for use in dissolving or suspending L-phenylalanine in the initial stage and in adjusting pH during the reaction, there may suitably be used the hydroxides, oxides, carbonates or hydrogen carbonates of alkali metals such as lithium, sodium and potassium, and the hydroxides, oxides, carbonates or hydrogen carbonates of alkaline earth metals such as calcium and magnesium. As a matter of course, no problems or difficulties will be encountered even if organic bases represented by triethylamine which are inactive to the anhydride are used.

Under the strongly alkaline conditions in which the pH of the reaction liquid exceeds 12, the ring opening reaction of N-formyl-L-aspartic acid anhydride by water or methanol is accelerated, thereby consuming an increased amount of N-formyl-L-aspartic acid anhydride and at the same time, unfavorably forming other by-products than the β-isomer. Further, an excessively acidic-sided pH during the reaction will cause the reaction with L-phenylalanine to retard unfavorably and the ring-opening reaction of the anhydride by water or methanol to take place preferentially.

The reaction temperature may be 50° C. or below, or preferably 30° C. or below, for the purpose of preventing the ring-opening of N-formyl-L-aspartic acid anhydride by water or methanol as far as possible. Although no particular restrictions are placed on its lower limit, it is advantageous to carry out the reaction at a temperature above −20° C. from the industrial standpoint. Further, in the condensation reaction, it is possible to use jointly organic solvents which are inactive to the reaction and do not interfere with the deposition of α-APM hydrochloride in the subsequent α-APM forming step.

Thus, N-formyl-α-L-aspartyl phenylalanine is formed as a primary product by the condensation reaction of N-formyl-L-aspartic acid anhydride with L-phenylalanine in water or water containing methanol. However, as mentioned above, its isomer, N-formyl-β-L-aspartyl phenylalanine is partly by-produced. The ratio of formation of the α-isomer to the β-isomer is usually in the range of 70:30–80:20 and the overall yield of the intended product and the β-isomer is generally 95% or more based on L-phenylalanine. The N-formyl-α-L-aspartyl-L-phenylalanine thus formed is not isolated in the process of the present invention, but the reaction mixture, as it is, is successively subjected to the α-APM forming step as described below.

In the second step of the process of the present invention, α-APM is produced successively in one reactor from the aforesaid condensation reaction liquid containing N-formyl-α-L-aspartyl-L-phenylalanine. Specifically, this can be accomplished by acidifying the reaction liquid with hydrochloric acid in the presence of methanol so as to bring it into contact with hydrochloric acid in the presence of methanol and thereby to precipitate the α-APM thus formed out of the reaction system as its hydrochloride.

To acidify the aforesaid condensation reaction mixture with hydrochloric acid, gaseous hydrogen chloride is introduced thereinto or concentrated hydrochloride acid solution is added thereto.

The resulting mixture is thus brought into contact with hydrochloric acid in the presence of methanol, thereby causing the deformylation and esterification of N-formyl-α-L-aspartyl-L-phenylalanine to proceed, with the result that α-APM is formed and deposited out of the system in the form of its hydrochloride.

The amount of methanol to be present in the reaction system in the α-APM forming step may be at least one equivalent relative to the N-formyl-α-L-aspartyl-L-phenylalanine formed in the condensation reaction, or preferably one equivalent or more relative to the starting L-phenylalanine. In relation to the upper limit of the amount of methanol, the use of unduly excessive amounts of methanol will cause the concentration of methanol in the reaction system to increase and thus the solubility of the α-APM hydrochloride formed in the reaction to be increased. In concequence, the α-APM hydrochloride is made difficult to deposit, and at the same time the α-APM formed is further esterified to unfavorably by-produce an increasing amount of α-L-aspartyl-L-phenylalaninem dimethyl ester. Therefore, methanol is generally used in an amount of 6 moles or less per mole of L-phenylalanine or preferably in a concentration of 30% by weight or less in terms of the concentration defined as [(methanol)/(methanol+HCl+H$_2$O)]×100.

Methanol may be added to the reaction liquid formed by the condensation of L-phenylalanine with N-formyl-L-aspartic acid anhydride either prior to or subsequent to its acidification with hydrochloric acid. However, when the condensation reaction is carried out in water containing methanol in an amount of one mole or more per mole of L-phenylalanine, it is possible to produce α-APM without further addition of methanol.

The amount of hydrochloric acid to be brought into contact with N-formyl-α-L-aspartyl-L-phenylalanine may be 1–10 equivalents to the starting L-phenylalanine. Further, a high yield of α-APM in the present invention is attained by depositing the α-APM formed by the reaction successively out of the system in the form of its hydrochloride. Therefore, the concentration of hydrochloric acid in the reaction system during the contact is also an essential factor in order to facilitate the deposition of α-APM hydrochloride. The concentration of hydrochloric acid is 3–33% by weight, or preferably 5–30% by weight in terms of the concentration defined as [(HCl)/(HCl+H$_2$O)].

If the concentration of hydrochloric acid is too low, the intended esterification is obstructed to a considerable extent. On the other hand, if the concentration of hydrochloric acid is excessively high, the α-APM hydrochloride formed is increased in solubility and is made hard to deposit out of the reaction system, so that the yield of α-APM is unfavorably decreased and the cleavage of the peptide linkage is liable to occur.

The temperature of the contact with hydrochloric acid is below the boiling point of the reaction mixture, or preferably 10°–60° C.

If the temperature is too low, the intended reaction including deformylation will be retarded and thus may take very long time to complete the reaction, which is not favorable from the industrial standpoint. On the other side, excessively high temperatures during the contact will not only bring about unfavorable side reactions such as the cleavage of the peptide linkage, but also increase the solubility of α-APM hydrochloride in the reaction system. As a result, α-APM hydrochloride is made hard to deposit out of the reaction system, resulting in the reduction in yield of α-APM.

In the process of the present invention, when the condensation reaction mixture is brought into contact with hydrochloric acid, a corresponding inorganic salt is formed by the neutralization between an alkali used in the condensation reaction and the hydrochloric acid. If the salt is precipitated out of the reaction system at the time of the contact, it is possible to separate it during the contact.

In the process of the present invention, the α-APM formed by the reaction is deposited out of the reaction system as its hydrochloride. Consequently, following the reaction, α-APM hydrochloride is isolated by filtration from the reaction mixture after it has been cooled as required. The α-APM hydrochloride thus isolated can be converted to free α-APM by neutralizing it in water in the state of suspension or solution with an alkali such as sodium hydroxide, sodium carbonate, sodium hydrogen carbonate or ammonia.

The present invention will hereinafter be described more specifically by the following examples. The analytical conditions of the high speed liquid chromatography employed in the examples are as follows:
Column: YMC pack A-312 6 mmφ×150 mm (filler: ODS)
Moving phase: 0.005 M/l aqueous sodium heptanesulfonate solution:methanol=65:35 (volume ratio) (pH is adjusted at 2.5 with phosphoric acid)
Flow rate: 1 ml/min.
Sensor: ultraviolet spectrometer

EXAMPLE 1

Into 66 g of water were dissolved 5.0 g of solid sodium hydroxide and then 19.8 g (0.12 mole) of L-phenylalanine and the resulting solution was cooled to 0° C. To the solution was charged slowly 18.8 g (0.13 mole) of N-formyl-L-aspartic acid anhydride at 0°–5° C. for 30 minutes. During the charge, 45% aqueous sodium hydroxide solution was added dropwise to the reaction liquid to keep its pH at 9–11. Thereafter, the reaction was conducted at the same temperature for one hour.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 75.4:24.6 while the overall yield of the two compounds was 96.8% based on L-phenylalanine.

To the reaction mixture was added 14.4 g of methanol and then was introduced 26.8 g of hydrogen chloride at a temperature below 55° C. The resulting reaction mixture was subjected to reaction at 50°–55° C. for one hour. Thereafter, the reaction mixture was cooled to 25° C. and subjected to further reaction at 20°–25° C. for 4 days.

Then, the reaction mixture was cooled below 5° C. and stirred at 0°–5° C. for 3 hours. The α-APM hydrochloride thereby precipitated was filtered and washed with cold water to obtain a wet cake of white α-APM hydrochloride. The wet cake was analyzed by high speed liquid chromatography, with the result that it contained 19.3 g of α-APM in a yield of 54.7% based on the starting L-phenylalanine.

EXAMPLE 2

The wet cake of α-APM hydrochloride obtained in Example 1 was suspended in 200 ml of water and neutralized at 20°–25 °C. with 20% aqueous sodium carbonate solution (pH =5.0). The resulting suspension was cooled to 5°C. stirred at the same temperature for one hour. The crystal thereby precipitated was filtered, washed with cold water and dried in vacuo to obtain 17.4 g of free α-APM.

Its analysis by high speed liquid chromatography revealed that no impurities were detected in the α-APM. The specific rotation of the α-APM was as follows: [α$_D^{20}$=16.07 (C=4, 15N formic acid)

EXAMPLE 3

Into 110 g of water were dissolved 7.0 g of flaky potassium hydroxide and then 19.8 g (0.12 mole) of L-phenylalanine and the resulting solution was cooled to 0° C. 18.8g (0.13 mole) of N-formyl aspartic acid anhydride was charged slowly to the resulting aqueous solution at 0°–5° C. for 30 minutes. During the charge, 16.0 g of 50% aqueous potassium hydroxide solution was simultaneously added dropwise to the reaction liquid to maintain its pH at 8–11. The reaction liquid was then stirred for one hour at the same temperature.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 77:23 while the overall yield of the two compounds was 98.9%.

To the reaction mixture was added 19.2 g of methanol and then was introduced 40.2 g of hydrogen chloride at a temperature below 55° C. The resulting reaction mixture was then subjected to reaction at 50°–55° C. for 30 minutes. Thereafter, the reaction mixture was cooled to room temperature and subjected to further reaction at room temperature for 5 days.

After the reaction, the reaction mixture was cooled below 5° C. and stirred at 0°–5° C. for 3 hours. The α-APM hydrochloride thereby precipitated was filtered and washed with cold water to obtain white α-APM hydrochloride. Its analysis by high speed liquid chromatography revealed that it contained 17.4 g of α-APM in a yield of 49.3% based on the starting L-phenylalanine.

EXAMPLE 4

In 66 g of water were dissolved 5.0 g of sodium hydroxide and then 19.8 g (0.12 mole) of L-phenylalanine and the resulting aqueous solution was cooled to $-5°$ C. Then, 18.8 g (0.13 mole) of N-formyl-L-aspartic acid anhydride was added little by little to the aqueous solution at a temperature below 10° C. for about one hour. During the addition, 19.0 g of 30% aqueous sodium hydroxide solution was added dropwise to the reaction liquid to keep its pH at 8-11. Thereafter, the reaction was conducted for one hour at the same temperature.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 76.1:24.9 while the overall yield of the two compounds was 97.4% based on the starting L-phenylalanine.

To the reaction mixture was added 8.3 g of methanol and then was introduced 35.9 g of hydrogen chloride at a temperature below 55° C. The resulting reaction mixture was subjected to reaction at 50°–55° C. for one hour and then cooled to 30° C. The reaction was further continued for 7 days at the same temperature.

After the reaction, the reaction mixture was treated in the same manner as described in Example 1, thereby obtaining α-APM hydrochloride which contained 20.5 g of α-APM in a yield of 58.1% based on the starting L-phenylalanine.

EXAMPLE 5

In 66 g of water were dissolved 14.4 g of methanol, 5.1 g of solid sodium hydroxide and further 19.8 g (0.12 mole) of L-phenylalanine, and the resulting solution was cooled to 0° C. 18.8 g (0.13 mole) of N-formyl-L-aspartic acid anhydride was added slowly to the solution at a temperature of 0°–5° C. for 30 minutes. During the addition, 45% aqueous sodium hydroxide solution was added dropwise to the reaction liquid to keep its pH at 9-12. Thereafter, the reaction was conducted for one hour at the same temperature.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 74.3:25.7 while the overall yield of the two compounds was 98.4% based on the starting L-phenylalanine.

29.5 g of hydrogen chloride was introduced into the reaction mixture at a temperature below 60° C. and the resulting reaction mixture was subjected to reaction at 50°–60° C. for one hour. The resulting reaction mixture was cooled to 25° C. and subjected to further reaction at 20°–25° C. for 4 days. The reaction mixture was then cooled below 5° C. and stirred at 0°–5° C. for 3 hours.

The α-APM hydrochloride thereby precipitated was filtered and washed with cold water to obtain a wet cake of white α-APM hydrochloride. The anaylsis of the wet cake by high speed liquid chromatography revealed that it contained 19.8 g of α-APM in a yield of 56.1% based on the starting L-phenylalanine.

EXAMPLE 6

The wet cake of α-APM obtained in Example 5 was suspended in 200 ml of water and neutralized at 20°–25° C. with 20% aqueous sodium hydroxide solution (pH=5.0). Thereafter, the suspension was cooled to 5° C. and stirred for one hour at the same temperature. The crystal thereby precipitated was filtered, washed with cold water and dried in vacuo to obtain 17.5 g of free α-APM.

Its analysis by high speed liquid chromatography revealed that no impurities were detected in the α-APM. The specific rotation of the α-APM was as follows: $[\beta_D^{20}] = 16.0$ (C=4, 15N formic acid)

EXAMPLE 7

In a mixed solvent consisting of 115 g of water and 19.2 g of methanol were dissolved 7.0 g of flaky potassium hydroxide and 19.8 g (0.12 mole) of L-phenylalanine, and the resulting aqueous solution was cooled to 0° C. 18.8 g (0.13 mole) of N-formyl-L-aspartic acid anhydride was added slowly to the aqueous solution at a temperature of 0°–5° C. for 30 minutes. During the addition, 15.5 g of 50% aqueous potassium hydroxide solution was simultaneously added dropwise to the reaction liquid to keep its pH at 8-11. The reaction liquid was then stirred for one hour at the same temperature.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 75.7:24.3 while the overall yield of the two compounds was 98.6%.

45.0 g of hydrogen chloride was introduced into the reaction mixture at a temperature below 55° C., and the reaction mixture was then subjected to reaction at 50°–55° C. for one hour. Thereafter, the reaction mixture was cooled to room temperature and subjected further reaction at room temperature for 6 days.

After the reaction, the reaction mixture was cooled below 5° C. and stirred at 0°–5° C. for 2 hours. The α-APM hydrochloride thus precipitated was filtered and washed with cold water to obtain white α-APM hydrochloride. The analysis of the α-APM hydrochloride by high speed liquid chromatography revealed that it contained 17.6 g of α-APM in a yield of 49.9% based on the starting L-phenylalanine.

EXAMPLE 8

In a mixed solvent consisting of 66 g of water and 7.7 g of methanol were dissolved 5.0 g of sodium hydroxide and 19.8 g (0.12 mole) of L-phenylalanine, and the resulting solution was cooled to 5° C. 18.8 g (0.13 mole) of N-formyl-L-aspartic acid anhydride was added little by little to the solution at a temperature below 10° C. for about one hour. During the addition, 30% aqueous sodium hydroxide solution (19.0 g) was added dropwise to the reaction liquid to keep its pH at 8-12. The reaction was continued for one hour at the same temperature.

A portion of the reaction liquid was analyzed by high speed liquid chromatography, with the result that the formation ratio of N-formyl-α-L-aspartyl-L-phenylalanine to N-formyl-β-L-aspartyl-L-phenylalanine was 74.8:25.2 while the overall yield of the two compounds was 97.8%.

Into the reaction mixture was introduced 31.0 g of hydrogen chloride at a temperature below 60° C. and the resulting reaction mixture was subjected to reaction at 50°–60° C. for one hour. The sodium chloride thus deposited was filtered and washed with a small amount of 20% hydrochloric acid. The filtrate and the washings were combined and subjected to reaction at 30° C. for 7 days.

After the reaction, the reaction mixture was treated in the same manner as described in Example 1, thereby obtaining α-APM hydrochloride which contained 19.4 g of α-APM in a yield of 55.0% based on the starting L-phenylalanine.

What is claimed is:

1. Process for preparing α-L-aspartyl-L-phenylalanine methyl ester or the hydrochloride thereof which comprises: condensating N-formyl-L-aspartic acid anhydride with L-phenylalanine in water present in an amount ten times or less that of the phenylalanine in the presence or absence of methanol in an amount of 6 moles or less per mole of the L-phenylalanine at a pH in the range of 7 to 12 to form N-formyl-α-L-aspartyl-L-phenylalanine; acidifying the reaction mixture successively with hydrochloric acid in the presence of methanol without isolating the N-formyl-α-L-aspartyl-L-phenylalanine so as to bring it into contact with hydrochloric acid in the presence of methanol, wherein the concentration of hydrochloric acid is 3 to 33 percent by weight in terms of the concentration defined as [HCl]/[HCl+H$_2$O], and the methanol is used in an amount of 1 to 6 moles per mol of L-phenylalanine, thereby to deposit α-L-aspartyl-L-phenylalanine methyl ester hydrochloride; separating the α-L-aspartyl-L-phenylalanine methyl ester hydrochloride; and neutralizing said hydrochloride as required.

2. The process as claimed in claim 1 wherein methanol is present in said condensation step.

* * * * *